US010545149B2

(12) United States Patent
Newman et al.

(10) Patent No.: US 10,545,149 B2
(45) Date of Patent: Jan. 28, 2020

(54) DETECTION OF HIV-RELATED PROTEINS IN URINE (75) Inventors: Gale W. Newman, Duluth, GA (US); Mike Powell, Douglasville, GA (US); Akins Doherty, Atlanta, GA (US); Chamberlain Obialo, Peachtree City, GA (US); Claudette Mitchell-Ali, Newnan, GA (US); Khalid Bashir, Dunwoody, GA (US); Mafuz Khan, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 489 days.

(21) Appl. No.: 12/572,652

(22) Filed: Oct. 2, 2009

(65) Prior Publication Data
US 2010/0086956 A1 Apr. 8, 2010

Related U.S. Application Data (60) Provisional application No. 61/102,941, filed on Oct. 6, 2008.

(51) Int. Cl.
*G01N 33/569* (2006.01)
*G01N 33/493* (2006.01)
*G01N 33/68* (2006.01)
*G01N 1/40* (2006.01)
*C07K 14/005* (2006.01)
*C07K 16/10* (2006.01)

(52) U.S. Cl.
CPC ...... *G01N 33/56988* (2013.01); *G01N 33/493* (2013.01); *G01N 33/6893* (2013.01); *C07K 14/005* (2013.01); *C07K 16/1054* (2013.01); *C07K 16/1063* (2013.01); *C07K 16/1072* (2013.01); *C12N 2740/16111* (2013.01); *C12N 2740/16211* (2013.01); *C12N 2740/16311* (2013.01); *G01N 1/40* (2013.01); *G01N 2333/161* (2013.01); *G01N 2333/162* (2013.01); *G01N 2333/163* (2013.01); *G01N 2800/347* (2013.01); *G01N 2800/56* (2013.01)

(58) Field of Classification Search
CPC ........... G01N 33/56988; G01N 33/493; G01N 2333/163; G01N 2333/162; G01N 2333/16; G01N 2333/161; C12N 2740/16211; C12N 2740/16311; C12N 2740/16111; C07K 16/1063; C07K 16/1054; C07K 16/1072; C07K 14/005
See application file for complete search history.

(56) References Cited

U.S. PATENT DOCUMENTS

| | | | | | |
|---|---|---|---|---|---|
| 5,256,561 | A | * | 10/1993 | Chin | C07K 14/005 435/339.1 |
| 5,462,852 | A | * | 10/1995 | Arthur | C07K 14/005 435/5 |
| 5,830,641 | A | * | 11/1998 | Montagnier | C07K 7/06 424/139.1 |
| 6,048,685 | A | * | 4/2000 | Alizon | C07K 7/06 435/5 |
| 6,194,142 | B1 | * | 2/2001 | Moncany | C07K 14/005 435/5 |
| 6,296,807 | B1 | * | 10/2001 | Montagnier | C07K 14/005 422/430 |
| 6,383,740 | B2 | * | 5/2002 | Collins | G01N 33/54306 435/5 |
| 7,198,923 | B1 | * | 4/2007 | Abrignani et al. | 435/91.1 |
| 2001/0039009 | A1 | * | 11/2001 | Chien et al. | C12Q 1/70 435/5 |
| 2003/0143248 | A1 | * | 7/2003 | Megede | C07K 14/005 424/208.1 |
| 2004/0241176 | A1 | * | 12/2004 | Lamparski et al. | 424/185.1 |
| 2006/0252075 | A1 | * | 11/2006 | Zagury et al. | 435/6 |
| 2009/0078638 | A1 | * | 3/2009 | Bonhomme et al. | 210/251 |
| 2010/0203529 | A1 | * | 8/2010 | Kuslich et al. | 435/6 |

FOREIGN PATENT DOCUMENTS

| | | | | | |
|---|---|---|---|---|---|
| EP | | 0400548 | * | 5/1990 | ........... G01N 33/569 |
| WO | WO | 2005/010143 | * | 2/2005 | |
| WO | WO | 2005/121369 | * | 12/2005 | ............... C12Q 1/68 |
| WO | | 2007/103572 A2 | | 9/2007 | |
| WO | WO | 2009092386 | * | 7/2009 | ........... G01N 33/569 |

OTHER PUBLICATIONS

Cheruvanky et al., "Rapid Isolation of urinary exosomal biomarkers using a nanomembrane ultrafiltration concentrator", Am J Physiol renal Physiol, 2007, vol. 292, No. 5, pp. 1-12.*
Tehe et al., "Quantification of HIV-1 p. 24 by a highly improved ELISA: An alternative to HIV-1 RNA based treatment monitoring in patients from Abidjan, Cote d'Ivoire", Journal of Clinical Virology, 2006, vol. 37, pp. 199-205.*
Schupbach et al., "Use of HIV-1 p. 24 as a sensitive, precise and inexpensive marker for infection, disease progression and treatment failure", International Journal of Antimicrobial Agents 2000, vol. 16, pp. 441-445.*
Li et al., "Detection of Human Immunodeficiency Virus Type 1 (HIV-1) in Urine Cell Pellets from HIV-1-Seropositive Individuals", Journal of Clinical Microbiology, May 1992, vol. 10, No. 5, pp. 1051-1055.*
Nguyen et al., "Evidence That HIV Budding in Primary Macrophages Occurs through the Exosome Release Pathway", The Journal of Biological Chemistry, 2003, vol. 278, No. 52, pp. 52347-52354.*
Van Niel et al., "Exosomes: A Common Pathway for a Specialized Function", Journal of Biochemistry, 2006, vol. 140, No. 1, pp. 13-21.*

(Continued)

*Primary Examiner* — Jeffrey S Parkin
(74) *Attorney, Agent, or Firm* — Ping Wang; Morris, Manning & Martin, LLP (57) ABSTRACT

A method for detecting HIV infection in a mammal is disclosed. The method contains the steps of isolating exosomes from a urine sample of a mammal and detecting the presence of HIV-specific biomarker in said isolated exosomes. A method for diagnosing a mammal with an HIV-associated disease, in particular, HIV-associated nephropathy is also disclosed.

8 Claims, 9 Drawing Sheets

(56) References Cited

OTHER PUBLICATIONS

Segura et al., "Identification of Host Proteins Associated with Retroviral Vector Particles by Proteomic Analysis of Highly Purified Vector Preparations", Journal of Virology 2008, vol. 82, No. 3, pp. 1107-1117.*
Barral et al., "Exosomes: Specific Intercellular Nano-Shuttles?", Current Immunology Reviews, 2005, vol. 1, No. 1, pp. 1-6.*
Johns Hopkins Bloomburg School of Public Health, 1999, http://www.jhsph.edu/news/news-releases/1999/hiv-urine-test.html, p. 1.*
Frankel, Alan D., "HIV-1: Fifteen Proteins and an RNA", Annu. Rev. Biochem., 1998, vol. 67, pp. 1-25.*
Wehrly et al., "p. 24 Antigen Capture Assay for Quantification of Human Immunodeficiency Virus using Readily Available Inexpensive Reagents", Methods: A Companion to Methods In Enzymology, 1997, vol. 12, pp. 288-293.*
Pineda et al., "A TRIM5alpha-independent post-entry restriction to HIV-1 infection of macaque cells that is dependent on the path of entry", Virology, 2007, vol. 363, pp. 310-318.*
Winston et al., "Kidney Disease in patients with HIV Infection and Aids", Clinical Infectious Diseases, electronically published Oct. 2008, vol. 47, pp. 1449-1457.*
Graziani et al., "Diagnostic accuracy of a reagent strip for assessing urinary albumin excretion in the general population", Nephrol Dial Transplant, Advance Access publication Nov. 26, 2008, vol. 24, pp. 1490-1494.*
Buonaguro, L., et al., 2001, High efficient production of Pr55gag virus-like particles expressing multiple HIV-1 epitopes, including a gp120 protein derived from an Ugandan HIV-1 isolate of subtype A, Antivir. Res. 49:35-47.*
Miyake, K., et al., 2007, Development of targeted gene transfer into human primary T lymphocytes and macrophages using high-titer recombinant HIV vectors, J. Biotech. 129:532-538.*
Reiser, J., et al., Dec. 1996, Transduction of nondividing cells using pseudotyped defective high-titer HIV type 1 particles, Proc. Natl. Acad. Sci. USA 93:15266-15271.*
Wyatt, C.M., et al., "HIV-Associated Nephropathy in the Era of Antiretroviral Therapy", American Journal of Medicine, vol. 120, pp. 488-492 (2007).
Wiley, R.D., et al., "Immature dendritic cell-derived exosomes can mediate HIV-1 trans infection", PNAS, vol. 103, pp. 738-743 (2006).
International Search Report and Written Opinion of the International Search Authority (International Application No. PCT/US2009/059600, filed Oct. 5, 2010).
Booth, A.M., et al., "Exosomes and HIV Gag bud from endosome-like domains of the T cell plasma membrane", the Journal of Cell Biology, vol. 172, pp. 923-935 (2006).
Fang, Y., et al., "Higher-Order Oligomerization Targets Plasma Membrane Proteins and HIV Gag to Exosomes", PLoA Biology, vol. 6, pp. 1267-1283 (1007).
Keller, S., et al., "Exosomes: From biogenesis and secretion to biological function", Immunology Letters, vol. 107, pp. 102-108 (2006).
Pelchen-Matthews, A., et al., "Endosomes, exosomes and Trojan viruses", Trends in Microbiology, vol. 12, pp. 310-316 (2004).
International Preliminary Report on Patentability (Application No. PCT/US2009/059500, filed Oct. 5, 2009).
Extended European Search Report dated Apr. 17, 2012 issued in European Patent Application No. 09819705.6.
Dimov, I., et al., "Urinary exosomes", The Scientific World Journal, vol. 9, pp. 1107-1118 (2009).
Hoorn, E.J., et al., "Prospects for urinary proteomics: exosomes as a source of urinary biomarkers", Nephrology, vol. 10, pp. 283-290 (2005).
Campbell, T.D., et al., "HIV-1 Nef protein is secreted into vesicles that can fuse with target cells and virions", Ethnicity & Disease, vol. 18, pp. S214-S219 (Spring 2008).
Simpson, R.J., et al., "Exosomes: proteomic insights and diagnostic potential", Expert Review Proteomics, vol. 6, Issue 3, pp. 267-283 (2009).
Simpson, R.J., et al., "Proteomic profiling of exosomes: current perspectives", Proteomics, vol. 8, pp. 4083-4099 (2008).
Soler-Garcia, A.A., et al., "A urinary biomarker profile for children with HIV-associated renal diseases", Kidney International, vol. 76, pp. 207-214 (2009).
Pisitkun, T., et al., "Identification and proteomic profiling of exosomes in human urine", PNAS, vol. 101, No. 36, pp. 13368-13373 (Sep. 7, 2004).

\* cited by examiner

HIV White

54 – 52 yr, M. CD4 550, VL 400, neg P

FIG.4A

HIV White

60 – 52 yr, M, CD4 450, VL 870, neg P

FIG.4B

HIV White

69 – 48 yr, M, CD4 187, VL < 50, neg P

FIG.4C

Renal 53 yr, B/M, neg P

FIG.5A

Renal 51 yr, B/F, 100 mg/dl P (2+)

FIG.5B

Renal 64 yr, B, CKD 3, 2000 mg/dl P (4+)

HIVAN (1:10 dilution)

FSGS

AA HIV+

White HIV+

AA HIV negative

DETECTION OF HIV-RELATED PROTEINS IN URINE

This application claims priority from U.S. Provisional Application Ser. No. 61/102,941, filed Oct. 6, 2008. The entirety of that provisional application is incorporated herein by reference.

This application was made with government support under certain grants awarded by the NIH. The government has certain rights in the application.

FIELD

The present invention generally relates to methods for diagnosis and, in particular, to methods for detecting HIV infection, diagnosing HIV or HIV-associated diseases using biomarkers in the urine.

BACKGROUND

HIV tests are generally performed on serum or plasma. The detection of a HIV antibody is presumptive evidence of HIV-1 infection, and is typically confirmed by the Western blot procedure. Detection of virus by p24 antigen determination or detection of viral RNA by RT-PCR is also used to determine the amount of virus in circulation. CD4/CD8 T cell ratios and other immune function tests are often used to monitor immune status and progression to AIDS. More recently, HIV tests using saliva or epithelia cells in the mouth have also been developed. However, currently there is no test available to measure antigen or antibody in urine. The detection of HIV proteins in the urine may provide a more rapid method to detect HIV infection or progression of disease, particularly renal complications.

HIV-Associated Nephropathy (HIVAN), a renal disease that disproportionately afflicts people of African descent, is characterized by kidney hypertrophy and rapid progression and stage renal disease. HIVAN is caused by direct infection of the renal cells with the HIV-1 virus and leads to renal damage through the viral gene products. It could also be caused by changes in the release of cytokines during HIV infection. The etiology of HIVAN is still unknown. It is estimated that 90% of HIVAN sufferers are people of African descent, suggesting a genetic predisposition to the disease (Wyatt, C. M., Klotman, P. E. HIV-Associated Nephropathy in the Era of Antiretroviral Therapy. *American Journal of Medicine Review* 2007).

Renal biopsies of patients showing focal segmental glomerulosclerosis with tubular dilation and inflammation, microcystic tubules, degenerating glomerular capillaries in conjunction with marked proteinuria is diagnostic for HIVAN (supra). This method, however, is an invasive procedure and is sometimes rejected by patients because of its invasiveness. Therefore, there exists a need for diagnostic test from HIV or an HIV associated disease that is reliable, rapid, cost-effective and less invasive.

SUMMARY

One aspect of the present invention relates to a method for detecting HIV infection in a mammal. In one embodiment, the method contains the steps of isolating exosomes from a urine sample of said mammal and detecting a HIV-associated biomarker from said isolated exosomes.

In a related embodiment, the method further comprises the step of determining whether the mammal is infected by HIV based on the presence or absence of HIV-associated biomarkers in the isolated exosomes.

In a related embodiment, the exosomes are isolated by centrifugation.

In another related embodiment, the exosomes are isolated by filtration.

In another related embodiment, the exosomes are detected by one or more techniques selected from the group consisting of: electrophoresis, Western blot, HPLC, FPLC, MS and protein sequencing.

In another related embodiment, the exosomes are detected by SELDI-TOF-MS and LC-MS/MS.

In another related embodiment, the HIV-associated biomarker is selected from the group consisting of Nef, HIV envelope gp120, HIV protease, Vif, Gag-Pol, Gag, p24, Rev, reverse transcriptase (RT), Tat, p1, p17, Vpu, Vpr, gp41 and DNA polymerase.

In another related embodiment, the HIV-associated biomarker is Nef, HIV protease, Vif, Pol or Gag.

In another related embodiment, the HIV-associated biomarker is Nef.

In one related embodiment, the mammal is a human, monkey, gorilla or baboon.

In another related embodiment, the mammal is a human.

Another aspect of the present invention relates to a method for diagnosing HIV-associated disease in a mammal. In one embodiment, the method contains the steps of isolating exosomes from a urine sample of said mammal and detecting a HIV-associated biomarker from said isolated exosomes.

In another related embodiment, said HIV-associated disease is HIV-associated nephropathy.

In another related embodiment, the method further comprises the step of determining whether the mammal is suffering from HIV-associated nephropathy based on the presence or absence of said HIV-associated biomarker in the isolated exosomes.

In one related embodiment, the mammal is a human, monkey, gorilla or baboon.

In another related embodiment, the mammal is a human.

Another aspect of the present invention relates to a method for monitoring the progress of HIV infection in a mammal. In one embodiment, the method contains the steps of isolating exosomes from a urine sample of the mammal and detecting said a HIV-associated biomarker from said isolated exosomes.

In another related embodiment, the method further comprises the step of determining the progress of HIV infection in said mammal based on the presence or absence of said HIV-associated biomarker in the isolated exosomes.

Another aspect of the present invention relates to a method for monitoring the progress of HIV-associated nephropathy in a mammal. In one embodiment, the method contains the steps of isolating exosomes from a urine sample from the mammal and detecting said a HIV-associated biomarker from said isolated exosomes.

In another related embodiment, the method further comprises the step of determining the progress of HIV-associated nephropathy in said mammal based on the presence or absence of said HIV-associated biomarker in the isolated exosomes.

Another aspect of the present invention relates to a method for monitoring the effectiveness of treatment to a mammal with an anti-HIV agent. The method includes the steps of determining a HIV-associated biomarker profile in urine exosomes in the urine sample obtained from a mammal prior to administration of an agent; determining a HIV-associated biomarker profile in urine exosomes in a one or more post-administration urine samples of said mammal; comparing the HIV-associated biomarker profile in the pre-administration sample with the HIV-associated biomarker profile in the post administration sample or samples; and determining the effectiveness of the agent.

In a related embodiment, the method further contains the step of altering the administration of the agent to said mammal.

Another aspect of the present invention relates to a kit for detecting HIV infection or monitoring the progress of HIV infection in a mammal. The kit contains one or more reagents for preparing exosomes sample for detection and at least one HIV-associated biomarker as a standard.

In another related embodiment, the exosomes are detected by Western blot.

In another related embodiment, the kit further includes a label.

In another related embodiment, the kit further includes a label with instruction.

Another aspect of the present invention relates to a kit for diagnosing a HIV-associated disease or monitoring the progress of a HIV-associated disease in a mammal. The kit contains one or more reagents for preparing exosomes sample for detection and at least one HIV-associated biomarker as a standard.

In another related embodiment, said HIV-associated disease is HIV-associated nephropathy.

In one related embodiment, the HIV-associated biomarker is selected from the group consisting of Nef, HIV envelope gp120, HIV protease, Vif, Gag-Pol, Gag, p24, Rev, reverse transcriptase (RT), Tat, p1, p17, Vpu, Vpr, gp41 and DNA polymerase.

In a further related embodiment, the HIV-associated biomarker is Nef, HIV protease, Vif, Pol, or Gag.

In a further related embodiment, the HIV-associated biomarker is Nef.

DETAILED DESCRIPTION

The practice of the embodiments described in further detail below will employ, unless other wise indicated, conventional methods of diagnostics, molecular biology, cell biology, biochemistry and immunology within the skill of the art. Such techniques are explained fully in the literature. All publications, patents and patent applications cited herein, whether supra or infra, are hereby incorporated by reference in their entirety.

Figure 1:
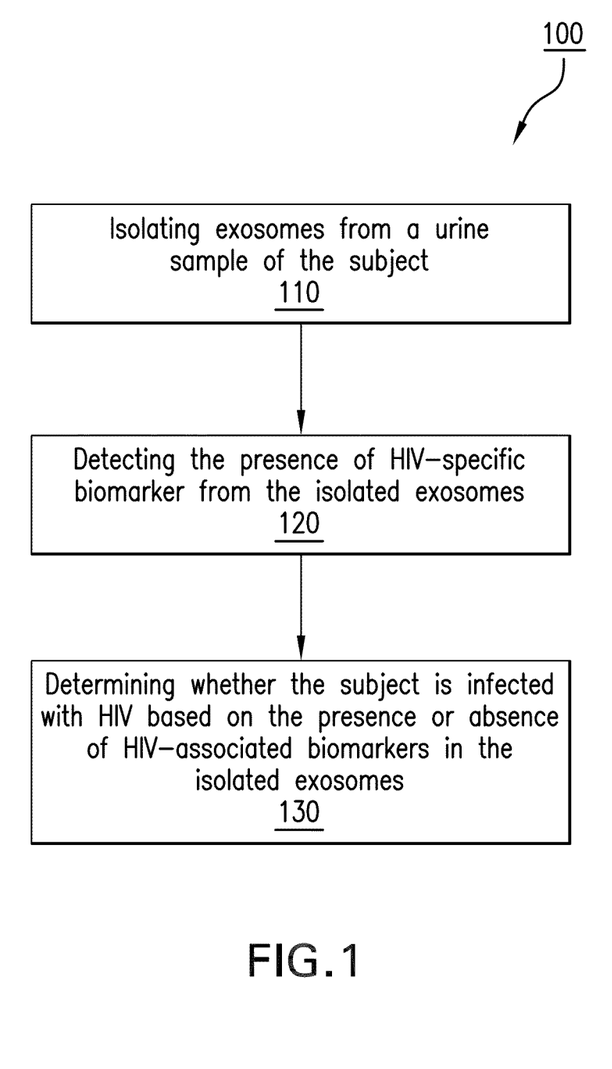
FIG. 1 is a flow chart showing an embodiment of a method for detecting HIV-infection or monitoring the progress of HIV-infection in a mammal using a urine sample from the mammal.
Figure 2A:
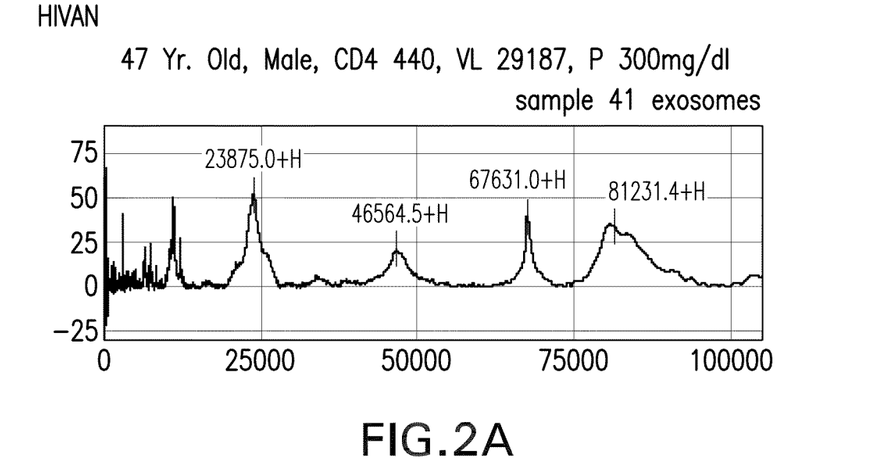
FIGS. 2A-2C are composites of samples SELDI-TOF-MS spectrum of urinary exosomes from patients in the HIVAN groups.
Figure 2B:
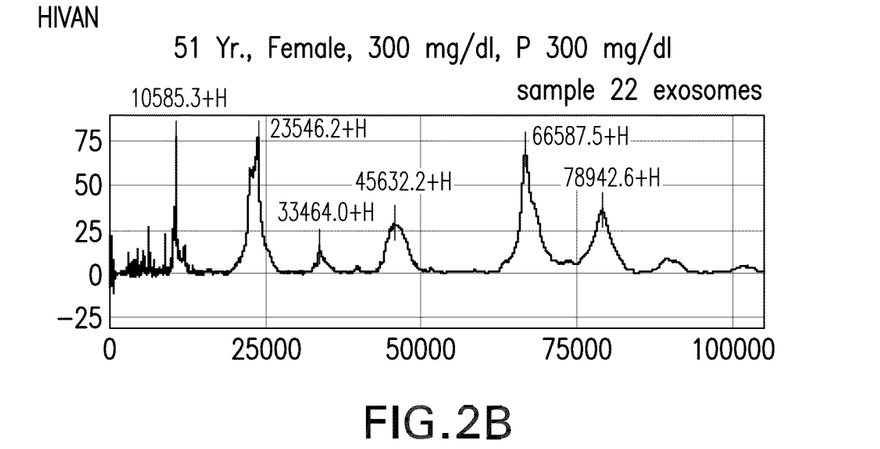
Figure 2C:
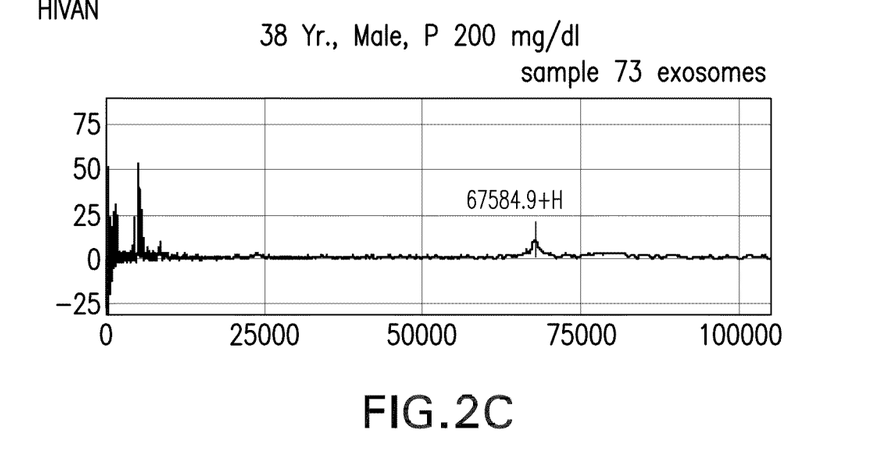
Figure 3A:
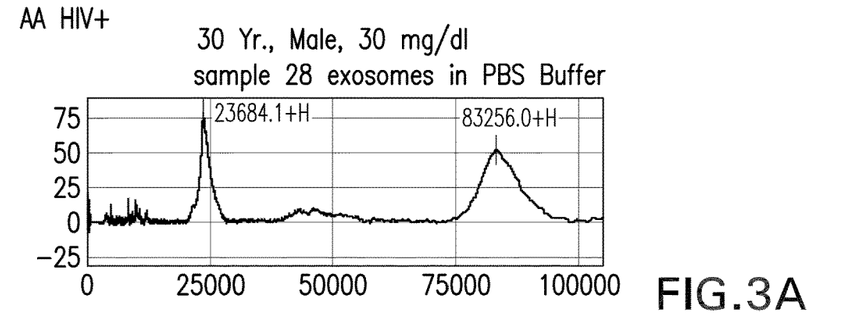
FIGS. 3A-3D are composites of samples SELDI-TOF-MS spectrum of urinary exosomes from patients in the AA HIV+ groups.
Figure 3B:
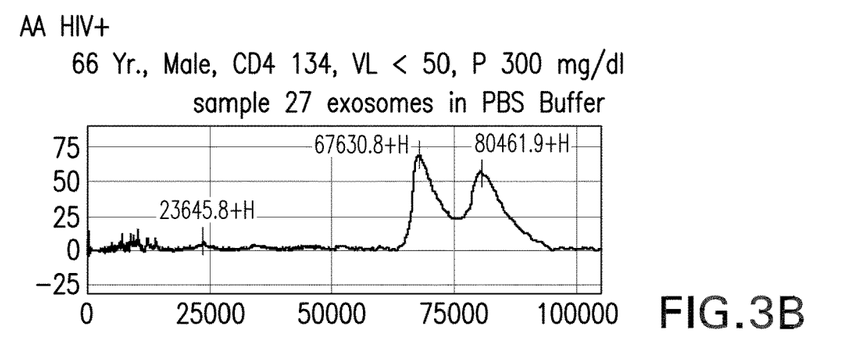
Figure 3C:
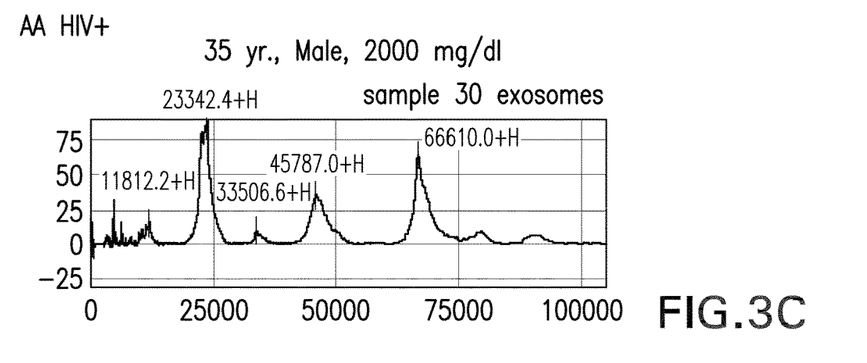
Figure 3D:
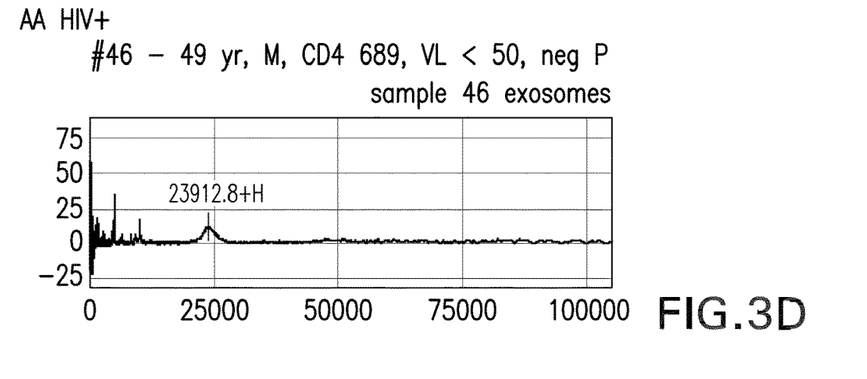
Figure 4A:
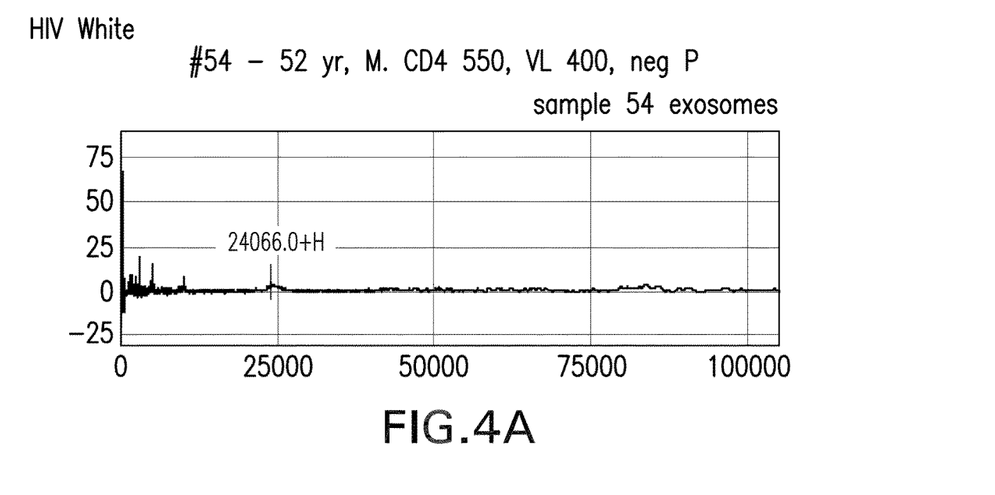
FIGS. 4A-4C are composites of samples SELDI-TOF-MS spectrum of urinary exosomes from patients in the HIV White groups.
Figure 4B:
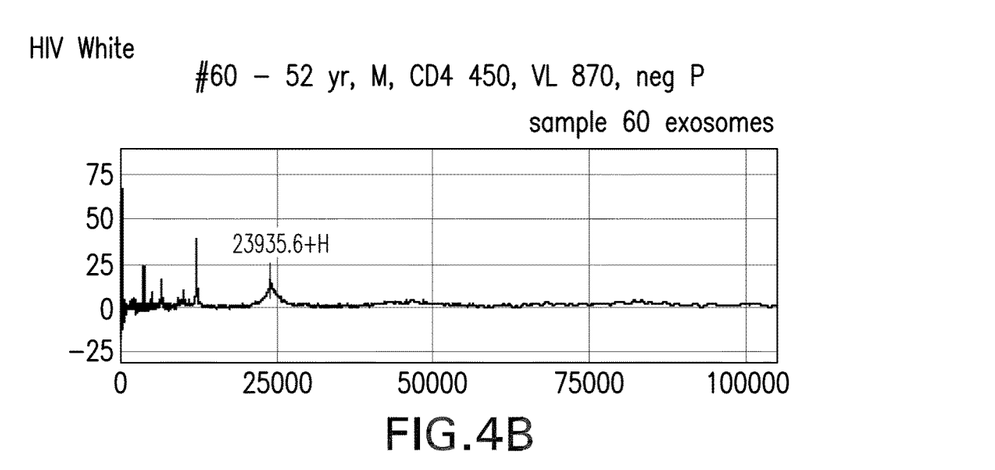
Figure 4C:
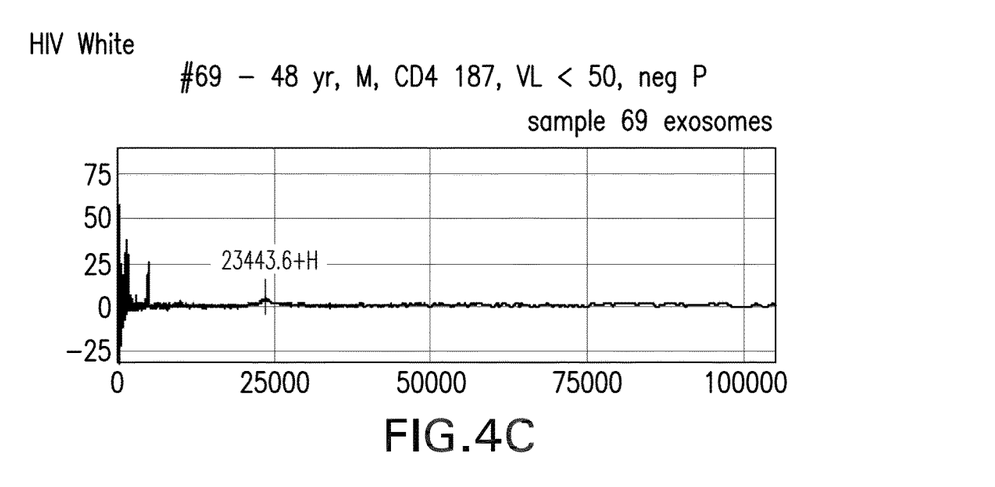
Figure 5A:
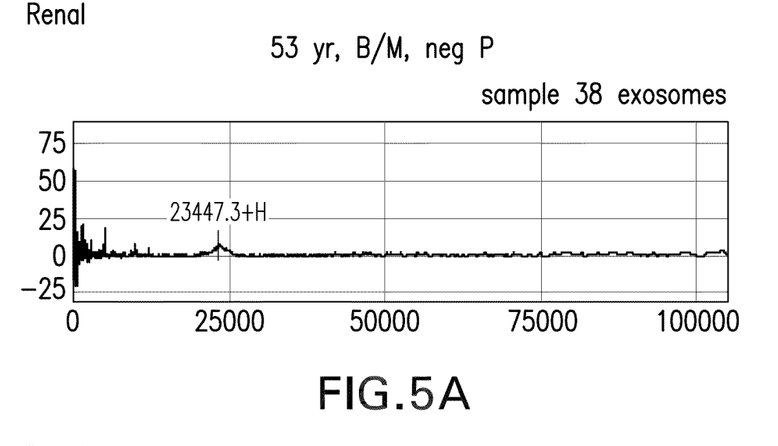
FIGS. 5A-5E are composites of samples SELDI-TOF-MS spectrum of urinary exosomes from patients in the FSGS groups.
Figure 5B:
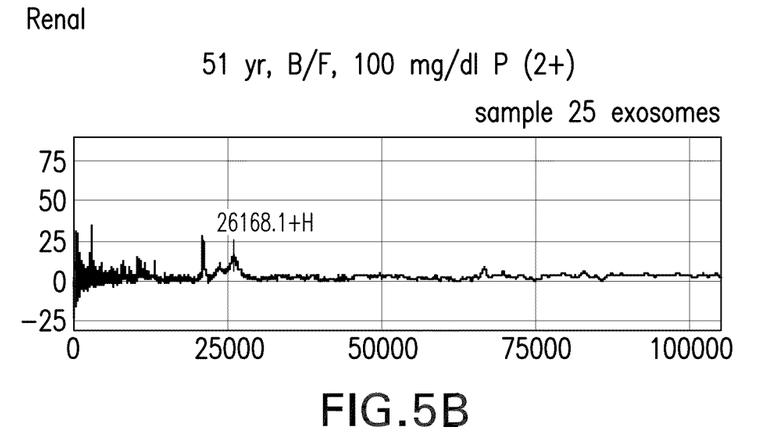
Figure 5C:
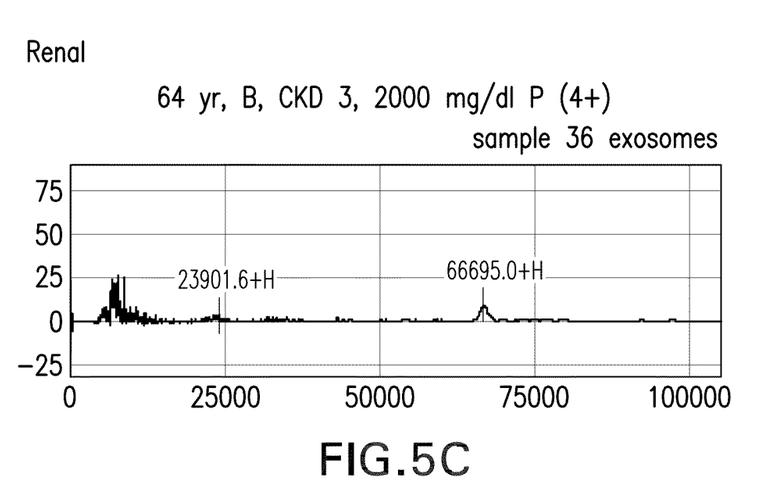
Figure 5D:
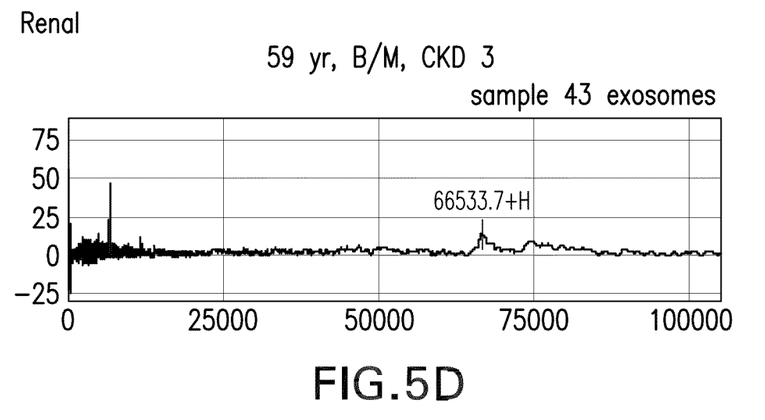
Figure 5E:
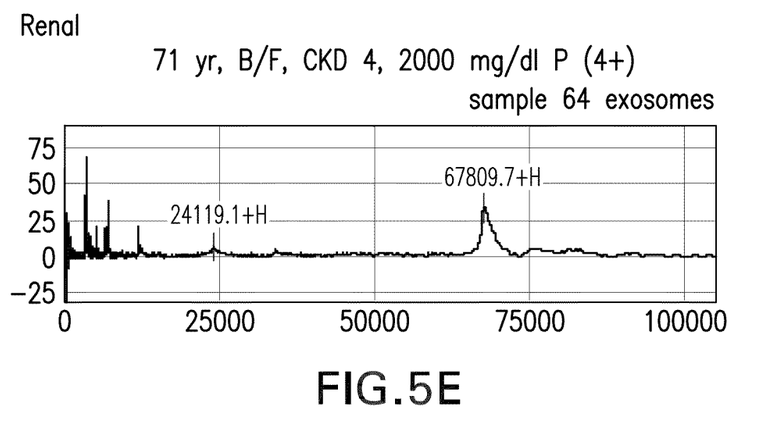
Figure 6A:
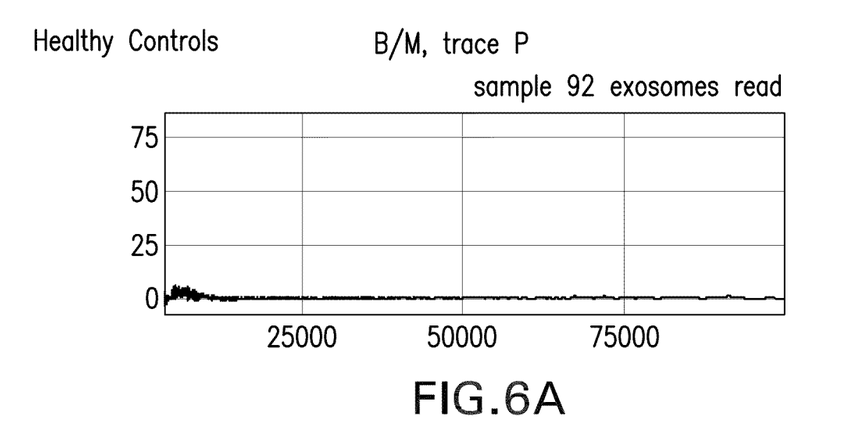
FIGS. 6A-6C are composites of samples SELDI-TOF-MS spectrum of urinary exosomes from patients in the Normal Controls groups.
Figure 6B:
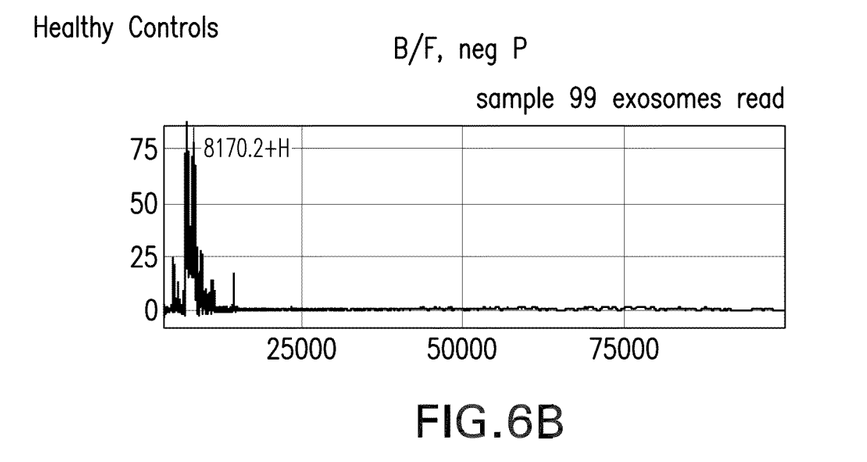
Figure 6C:
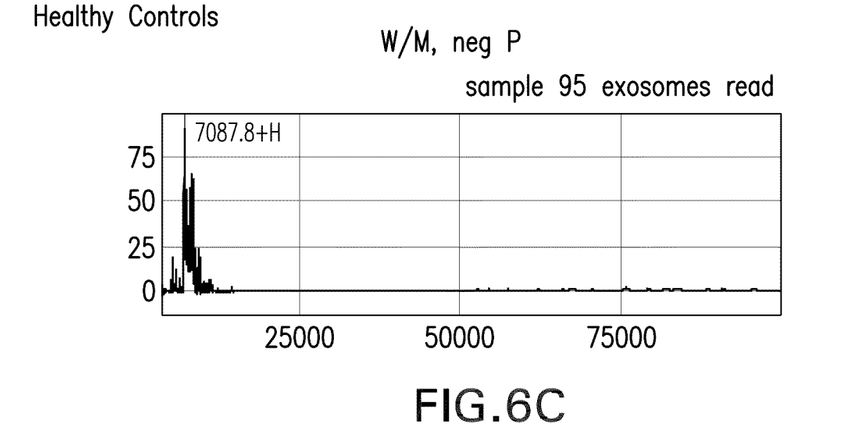
Figure 7A:
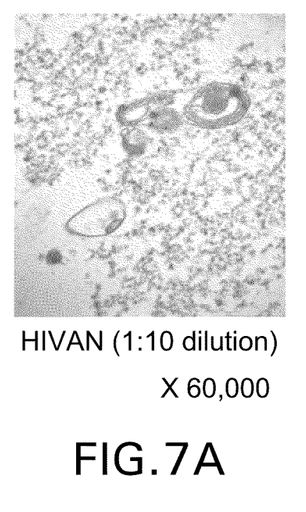
FIGS. 7A-7E are composites of transmission electron microscope (TEM) pictures of urinary exosomes isolated from patients from the HIVAN group (Figure A), the FSGS group (Figure B), the African American (AA) HIV+ group (Figure C), the white HIV+ group (Figure D), and the normal control group (Figure E).
Figure 7B:
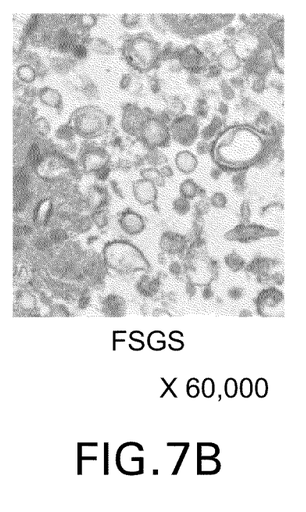
Figure 7C:
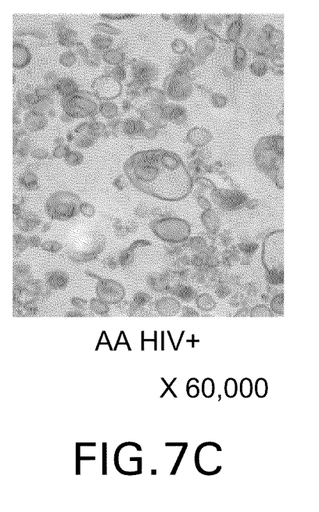
Figure 7D:
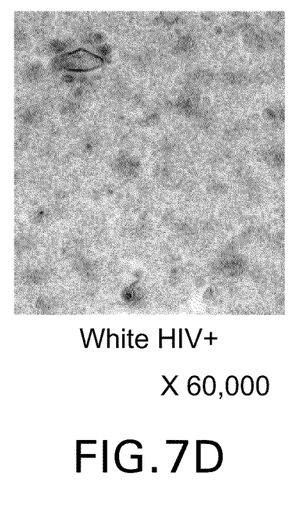
Figure 7E:
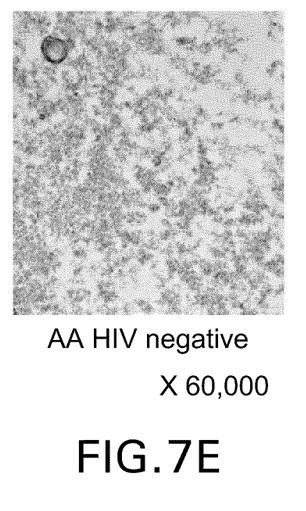

One aspect of the present invention relates to a method for detecting HIV infection in a mammal. As shown in FIG. 1, an embodiment of the method 100 includes the steps of: isolating (110) exosomes from a urine sample of a mammal and detecting (120) the presence of an HIV-associated biomarker from the isolated exosomes.

In one embodiment, the method may further comprise the step of determining (130) whether the mammal is infected with HIV based on the presence or absence of HIV-associated biomarkers in the isolated exosomes.

Exosomes are 50-90 nm vesicles secreted by a wide range of mammalian cell types. First discovered in maturing mammalian reticulocytes, they were shown to be a mechanism for selective removal of many plasma membrane proteins. An exosome is created intracellularly when a segment of the cell membrane spontaneously invaginates and is endocytosed. The internalized segment is broken into smaller vesicles that are subsequently expelled from the cell. The latter stage occurs when the late endosome, containing many small vesicles, fuses with the cell membrane, triggering the release of the vesicles from the cell. The vesicles (once released are called exosomes) consist of a lipid raft embedded with ligands common to the original cell membrane.

Although the exosomal protein composition varies with the cell of origin, most exosomes contain the soluble protein Hsc 70. Certain immune cells, such as dendritic cells and B cells, secrete exosomes that many scientists believe play a functional role in mediating adaptive immune responses to pathogens and tumors. It has been reported that immature dendritic cell-derived exosomes can mediate HIV trans infection (Wiley R D et al., *Proc Natl Acad Sci U.S.A.* 2006 Jan. 17; 103(3): 738-743).

The isolating step 110 can be accomplished by centrifugation or filtration. In one embodiment, exosomes in a urine sample are sedimented by centrifugation. The sedimented exosomes are washed and resuspended at a proper concentration for further analysis. In certain embodiments, the urine sample is centrifuged at 100,000×g or above for 10-120 minutes to sediment the exosomes. In one embodiment, the urine sample is centrifuged at 100,000×g for 60-120 minutes to sediment the exosomes.

In certain other embodiments, the exosomes in the urine sample are precipitated by a two-step centrifugation process that includes a low g force centrifugation to remove calls and other large particles in the urine and a high g force centrifugation to precipitate the exosomes. In one embodiment, the urine sample is first centrifuged at 5,000-25,000×g for 5-30 minutes. The supernatant is then transferred to another tube and is centrifuged again at 100,000×g or above for 30-120 minutes to sediment the exosomes. In a preferred embodiment, the urine sample is first centrifuged at 20,000-22,000×g for 10-20 minutes. The supernatant is then transferred to another tube and is centrifuged again at 100,000×g for 30-90 minutes to sediment the exosomes. The sedimented exosomes are then resuspended in a liquid medium for further analysis.

The liquid medium can be isotonic, hypotonic, or hypertonic. In certain embodiments, the liquid medium contains a buffer and/or at least one salt or a combination of salts. Buffers can maintain pH within a particular range, for example, between 1 and 12, and are also referred to as pH stabilizing agents. More typically, pH will range within about pH 5.0 to about pH 12.0. A particular example of a pH stabilizing agent is a zwitterion. Specific non-limiting examples of pH stabilizing agents include Tris(hydroxymethyl)aminomethane hydrochloride (TRIS), N-(2-hydroxyethyl)piperazine-N'-2-ethanesulfonic acid (HEPES), 3-(N-morpholino) propanesulfonic acid (MOPS), 2-(N-morpholino) ethanesulfonic acid (MES), N-tris[hydroxymethyl] methyl-2-aminoethanesulfonic acid (TES), N-[carboxymethyl]-2-aminoethanesulfonic acid (ACES), N-[2-acetamido]-2-iminodiacetic acid (ADA), N,N-bis[2-hydroxyethyl]-2-aminoethanesulfonic acid (BES), N-[2-hydroxyethyl]piperazine-N-[2-hydroxypropoanesulfonic acid] (HEPPSO), N-tris[hydroxymethyl]methylglycine (TRICINE), N,N-bis[2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), piperazine-N,N'-bis(2-ethanesulfonic acid (PIPES), [(2-hydroxy-1,1-bis[hydroxymethyl]ethyl)amino]-1-propanesulfonic acid (TAPS), N-tris(hydroxymethyl)methyl-4-aminobutane sulfonic acid (TABS), 2-amino-2-methyl-1-propanol (AMP), 3-[(1,1-dimethyl-2-hydroxyethyl)amino]-2-hydroxypropanesulfonic acid (AMPSO), ethanolamine and 3-amino-1-propanesulfonic acid. Additional specific non-limiting examples of pH stabilizing agents include potassium chloride, citric acid, potassium hydrogenphthalate, boric acid, potassium dihydrogenphosphate, diethanolamine, sodium citrate, sodium dihydrogenphosphate, sodium acetate, sodium carbonate, sodium tetraborate, cacodylic acid, imidazole, 2-Amino-2-methyl-1-propanediol, tricine, Gly-Gly, bicine, and a phosphate buffer (e.g., sodium phosphate or sodium-potassium phosphate, among others).

Buffers or pH stabilizing agents are typically used in a range of about 0.1 mM to about 500 mM, in a range of about 0.5 mM to about 100 mM, in a range of about 0.5 mM to about 50 mM, in a range of about 1 mM to about 25 mM, or in a range of about 1 mM to about 10 mM. More particularly, buffers can have a concentration of about (i.e., within 10% of) 1 mM, 2 mM, 5 mM, 10 mM, 15 mM, 20 mM, 25 mM, 30 mM, 40 mM, or 50 mM.

The liquid medium may further contain a chelating agent. Chelating agents typically form multiple bonds with metal ions, and are multidentate ligands that can sequester metals. Metal sequestration can in turn reduce or prevent microbial growth or degradation of biomolecules (e.g., peptide or nucleic acid), which in turn can improve preservation of biomolecules absorbed to a substrate. Specific non-limiting examples of chelating agents include EDTA (Ethylenediamine-tetraacetic acid), EGTA (Ethyleneglycol-O,O'-bis(2-aminoethyl)-N,N,N',N'-tetraacetic acid), GEDTA (Glycoletherdiaminetetraacetic acid), HEDTA (N-(2-Hydroxyethypethylenediamine-N,N',N'-triacetic acid), NTA (Nitrilotriacetic acid), Salicylic acid, Triethanolamine and porphines. Typical concentrations of chelating agents are in a range of about 0.1 mM to about 100 mM, in a range of about 0.5 mM to about 50 mM, or in a range of about 1 mM to about 10 mM.

The liquid medium may also contain a denaturing agent. Denaturing agents and detergents typically form a chemical bridge between hydrophobic and hydrophilic environments, which in turn disrupt or diminish the hydrophobic forces required to maintain native protein structure. Particular non-limiting chemical classes of denaturing agents and detergents include anionic surfactants, nonionic surfactants, cationic surfactants and ampholytic surfactants. Specific non-limiting examples of detergents include guanidinium thiocyanate, SDS, Sodium lauryl sulfate, NP40, triton X-100, Tween, Sodium cholate, Sodium deoxycholate, Benzethonium chloride, CTAB (Cetyltrimethylammonium bromide), Hexadecyltrimethylammonium bromide, and N,N-Dimethyldecylamine-N-oxide.

The liquid medium may further contain a denaturing agent. Reducing agents and antioxidants typically inhibit microbial growth and reduce biomolecule oxidation. Particular non-limiting classes of such agents include free radical scavenging agents. Specific non-limiting examples of reducing agents and anti-oxidants include DTT (dithiothreitol), dithioerythritol, urea, uric acid, 2-mercaptoethanol, dysteine, vitamin E, vitamin C, dithionite, thioglycolic acid and pyrosulfite.

The liquid medium may further contain a preservative or stabilizing agent. Preservatives or stabilizing agents can be used if it is desired to inhibit or delay degradation of an HIV-associated biomarker. Specific non-limiting examples of preservatives and stabilizing agents include sodium azide and polyethylene glycol (PEG). Typical concentrations of preservatives and stabilizing agents range from about 0.05% to about 1%.

The liquid medium may further contain a protease inhibitor. Protease inhibitors inhibit peptide degradation. Particular non-limiting classes of protease inhibitors include reversible or irreversible inhibitors of substrate (e.g., peptide) binding to the protease. Particular non-limiting classes of protease inhibitors include serine and cysteine protease inhibitors. Specific non-limiting examples of protease inhibitors include PMSF, PMSF Plus, APMSF, antithrombin III, Amastatin, Antipain, aprotinin, Bestatin, Benzamidine, Chymostatin, calpain inhibitor I and II, E-64,3,4-dichloroisocoumarin, DFP, Elastatinal, Leupeptin, Pepstatin, 1,10-Phenanthroline, Phosphoramidon, TIMP-2, TLCK, TPCK, trypsin inhibitor (soybean or chicken egg white), hirustasin, alpha-2-macroglobulin, 4-(2-aminoethyl)-benzenesulfonyl fluoride hydrochloride (AEBSF) and Kunitz-type protease inhibitors.

In another embodiment, exosomes in a urine sample are collected by passing the urine sample through a filter having a pore size that is smaller than the average size of exosomes. The exosomes are then removed from the filter and resuspended at a proper concentration for further analysis. In certain embodiments, exosomes in the urine samples are collected using centrifuge filters with a molecular weight cutoff of 500 kd-50 kd. In one embodiment, exosomes in the urine samples are collected using centrifuge filters with a molecular weight cutoff of 100 kd.

The detecting step 120 can be performed using any technology that is capable of identifying a HIV-associated biomarker. As used herein, the term "HIV-associated biomarker" refers to proteins or fragments of proteins that are associated with HIV infection, the progress of HIV infection, and HIV-related diseases such as HIV-associated nephropathy. Examples of HIV-associated biomarker include, but are not limited to, HIV proteins such as HIV envelope gp120/gp41, HIV protease, Nef, Vif, Gag-Pol, Gag, p24, Rev, reverse transcriptase, Tat, p1, p17, Vpr, Vpu and DNA polymerase.

A number of technologies can be used to identify a HIV-associated biomarker. Examples of such technologies include, but are not limited to, electrophoresis such as one-dimensional and two-dimensional gel analysis, Western blot, ELISA, HPLC, FPLC, mass spectrometry, protein sequencing, antibody array and combinations thereof. In one embodiment, the biomarkers are identified by Western blot. In another embodiment, the biomarkers are identified by Surface Enhanced Laser Desorption/Ionization Time of Flight Mass Spectrometry (SELDI-TOF-MS) and LC-MS/MS.

The determining step is carried out by comparing the HIV-associated biomarker profile in a urine sample to HIV-associated biomarker profiles stored in a database. A diagnosis is made based on the result of the comparison. A HIV-associated biomarker profile may contain from zero to multiple HIV-associated biomarkers. For example, the HIV-associated biomarker profile of a healthy mammal may contain no HIV-associated biomarkers. On the other hand, the HIV-associated biomarker profile of a patient with HIVAN may contain a plurality of HIV-associated biomarkers.

In one embodiment, the method 100 is used to monitor the progress of HIV infection in the mammal. In this embodiment, pertinent information from the medical record of the mammal may also be used in the determining step 130 to make a diagnosis.

In another embodiment, the method 100 is used for diagnosing HIV-associated nephropathy in a mammal. In this embodiment, the genetic background and pertinent information from the medical record of the mammal may also be used in the determining step 130 to make a diagnosis. In another embodiment, the method 100 may also be used to monitor the progress of HIV-associated nephropathy in the mammal.

In another embodiment, the method 100 is used to monitor effects during clinical trials of HIV-treatment. In such clinical trials, the HIV-associated biomarker profile in urine exosomes can be used as a readout, indicative of the physiological response of a mammal to the treatment.

In one related embodiment, a mammal is a human, monkey, gorilla or baboon.

In a preferred related embodiment, the mammal is a human.

Another aspect of the present invention provides a method for monitoring the effectiveness of treatment of a mammal with an anti-HIV agent. In one embodiment, the method includes the steps of: detecting the HIV-associated biomarker profile in urine exosomes in the sample obtained from a mammal prior to administration of the agent; detecting the HIV-associated biomarker profile in urine exosomes in one or more post-administration samples obtained from the mammal; comparing the HIV-associated biomarker profile in the pre-administration sample with the HIV-associated biomarker profile in the post administration sample or samples.

In another embodiment, the method further comprises the step of determining the effectiveness of the agent and optionally altering the administration of the agent to the mammal. According to such an embodiment, the HIV-associated biomarker profile may be used as an indicator of the effectiveness of an agent, even in the absence of an observable phenotypic response.

Another aspect of the present invention relates to a kit for detecting HIV infection or monitoring the progress of HIV infection in a mammal. The kit contains one or more reagents for preparing exosomes sample for detection and at least one HIV-associated biomarker as a standard.

In another related embodiment, the exosomes are detected by Western blot.

Another aspect of the present invention relates to a kit for diagnosing a HIV-associated disease or monitoring the progress of a HIV-associated disease in a mammal. The kit contains one or more reagents for preparing exosomes sample for detection and at least one HIV-associated biomarker as a standard.

In another related embodiment, the HIV-associated disease is HIV-associated nephropathy.

In another related embodiment, the HIV-associated biomarker is selected from the group consisting of Net HIV envelope gp120, HIV protease, Vif, Gag-Pol, Gag, p24, Rev, reverse transcriptase (RT), Tat, p1, p17, Vpu, Vpr, gp41 and DNA polymerase.

The kits described above typically include a label or packaging insert including a description of the components or instructions for use. Exemplary instructions include, instructions for collecting a urine sample, for harvesting exosomes from the urine, and for detecting an HIV-associated biomarker. The kits described above may additionally include a liquid suitable for resuspending the exosomes isolated from the urine sample. The kits described above may contain a container for collecting a urine sample and/or a centrifuge filter for isolating exosomes from the urine sample.

The present invention is further illustrated by the following examples which should not be construed as limiting. The contents of all references, patents and published patent applications cited throughout this application, as well as the Figures and Tables, are incorporated herein by reference.

EXAMPLE 1

Materials and Methods

Patients

HIV+ patients, at various stages of disease, were recruited for this study from four clinical sites in the Atlanta metropolitan area. Only those patients on dialysis were excluded from this study. All samples were collected in accordance with protocols approved by the Institutional Review Board and the Human Subjects Research Committee at Morehouse School of Medicine, and informed consent was obtained from all patients and healthy volunteers according to the guidelines instituted by the Institutional Review Board. Patients were divided into five groups: African American patients with HIV (AA HIV+), white patients with HIV (White HIV+), patients with HIVAN (HIVAN), African American patients with no HIV but FSGS, and healthy controls. Pertinent information was also collected from the medical record of the patients.

Sample Collection and Storage

Urine samples were collected from patients during routine clinical visits. Clinical data were obtained from the medical record of the patients. Urine was collected in sterile containers and transported back to the laboratory. Urinalysis was performed on each specimen using a Multistix 10 SG Reagent Strip (Bayer Corporation, Elkhart, Ind.) and the albumin to creatinine ratio determined by a Siemens Clinitek Microalbumin dipstick (Bayer Corp.). The strips were read on a Siemens Clinitek Status instrument (Bayer Corp.). Samples were centrifuged at 2,000×g for 10 minutes to remove whole cells and sediment. The remaining urine samples were aliquoted into 4 ml volumes and stored at −80° C. until they were analyzed.

Isolation of Exosomes

Two methods were evaluated for the isolation of exosomes, either high speed ultracentrifugation or ultrafiltration using a molecular weight cutoff filter. For the ultracentrifugation method, 4 ml of urine were transferred into a polycarbonate centrifuge tube and centrifuged at 21,000×g for 15 minutes. The supernatant was removed and again centrifuged at 100,000×g for 60 minutes to sediment the exosomes. The excess urine was decanted and the pellet was reconstituted in 100 μl phosphate buffered saline (PBS) and stored at 4° C. For the ultrafiltration method, 4 ml of urine were added to an Amicon Ultra centrifugal filter device (Ultracel, 100k cutoff, Millipore, Inc.) and centrifuged at 4,000×g for 20 min in a swinging bucket rotor. One hundred μl of PBS was used to rinse the filter and dilute the retentate. The protein concentration was determined using the bicinchoninic acid protein assay (Pierce).

Surface Enhanced Laser Desorption/Ionization Time of Flight Mass Spectrometry

Normal phase chips (ProteinChip NP20; Ciphergen Biosystems, Fremont, Calif.), that bind proteins through hydrophilic and charged residues were used for the analysis. Five μl of vesicle preparation was applied in duplicate to the chip and incubated for 30 minutes in a humid chamber. Chips were washed three times with 5 μl high-performance liquid chromatography (HPLC)-grade water and air dried for 10 minutes. Saturated sinapinic acid (SPA, Ciphergen Biosystems, CA) were prepared in 50% acetonitrile/0.5% trifluoroacetic acid according to manufacturers instructions. One μl of matrix solution (SPA) to each spot and air-dried and subsequently read with the ProteinChip Reader II, (Ciphergen Biosystems) using the following settings: laser intensity 250; detector sensitivity 10; high mass 300 Kda, optimized from 3 Kda to 50 Kda. The data acquisition method was set to automatic laser adjustment and peaks were auto identified from 3 Kda and 50 Kda.

LC-MS/MS Collected exosomes were analyzed by LC/MS using an LTQ mass spectrometer (ThermoFinnigan). The pelleted exosomes were first extracted with 2 D gel loading buffer (Q-biosciences) made fresh the day of analysis. The solubilized pellet was then precipitated using four volumes of ice-cold (−20° C.) acetone and incubated overnight at −20° C. The precipitate was collected by centrifugation at 19,200×g. The pellet was dried and re-dissolved into 50 mM ammonium bicarbonate (AmBIC). The protein solution was first reduced using 2 μl of a 500 mM stock of DTT (Q biosciences, single use) at 56° C. for 30 minutes. The solution was then alkylated by adding 2 μl of a 1M stock of iodacetic acid (IAA; Q-biosciences, single use) and incubating at room temperature for 30 minutes in the dark. A fresh vial of trypsin (Promega Gold mass spec grade) was diluted 8 ul to 312 ul in 50 mM AmBic and kept on ice. Ten microliters of the diluted trypsin was then added to the reaction and it was incubated at 37° C. for 4 hours with shaking. Then 50 ul of 0.5% formic acid was added and the mixture was either directly analyzed or stored at −20° C. for analysis. Ten microliters of sample was injected using an automated sampler onto a captrap (Michrom) C18 peptide trap at a flow of 10 μl per min. After 10 min the flow was switched to a 0.5 mm×50 micron C18 column (Microm). Peptides were eluted using a linear gradient of 5-40% acetonitrile in water over 50 min. The eluted peptides were directly introduced into an LTQ mass spectrometer using microspray ionization (Michrom Advance) at a flow rate of approximately 3 μl per min. Samples were analyzed using Excalibur 2.2 software set to analyze ions in a data dependent scanning mode. A precursor scan was was followed by data dependent scans of the three most intense ions. Files were searched against a subset of the NR database that included Human and HIV proteins using BioWorks 3.1 (ThermoFinnigan). The threshold for DTA generation was set at 200 and the tolerance for peptides was set at 0.5 Da and proteins at 1.0 Da. Initial protein identification lists were generated using consensus scores of >10.0 and Xcorr scores >1.0.

Electrophoresis and Western Blot

SDS PAGE electrophoresis. Samples were heated at 85° C. for 2 minutes in a Tris-Glycine SDS sample reducing buffer and loaded in a 4-12% Criterion XT Bis-Tris precast acrylamide gel (BioRad, Hercules, Calif.). Approximate 200 ng of sample were loaded into each well. Controls consisted of recombinant HIV Nef (gift of Dr. Andrea Raymond) and HIV recombinant p24 (Immunodiagnostics, Inc.) that were loaded at 30 to 40 ng per well. The gels were stained using Gel Code Blue (Pierce, Inc.) or the proteins were transferred to PVDF membrane (Immobilon-P, Millipore Corp, Billerica, Mass.) for western blot analysis. The SNAP ID system (Millipore, Corp) was used for the western blot analysis for the presence of either HIV Nef or HIV proteins. HIV Nef identification was performed using a monoclonal mouse anti-HIV Nef monoclonal antibody (1:1500, Chemicon Int., CA) and a secondary antibody, goat anti-mouse IgG (H+L) peroxidase conjugated antibody (1:15,000, Jackson Immunoresearch, West Grove, Pa.). HIV proteins were detected using pooled human HIV+ serum (1:15,000) as the primary antibody and a goat anti-human IgG (H+L) peroxidase conjugated antibody (1:15,000, Jackson Immunoresearch). The membrane was incubated with a chemiluminescent substrate (SuperSignal West Femto Maximum, Pierce, Inc.) and exposed to X-ray film (CL-Xposure, Kodak) and developed.

Transmission Electron Microscopy

Samples were fixed in 2.5% glutaraldehyde in 0.1M cacodylate buffer for 2 hours at 4 C followed by 2 washes with 0.1M cacodylate buffer, 5 minutes each. The samples were fixed again with 1% osmium tetroxide in 0.1M cacodylate buffer for 1 hour at 4° C. followed by 2 washes with the cacodylate buffer and 3 washes with deionized water, 5 minutes each. Thin sections were cut, stained with 0.5% aqueous uranyl acetate for 2 hours at room temperature, and viewed with a JEOL 1200EX transmission electron microscope.

EXAMPLE 2

Isolation of Urinary Vesicles, Ultracentrifugation Versus Ultrafiltration

Vesicles from the urine of six (6) different HIV+ patients were isolated by ultracentrifugation or ultrafiltration to determine which of the two methods yielded the greatest amount of protein. The ultrafiltration method consistently isolated more protein, 2930 μg (median), than the ultracentrifugation method, 591 μg (median).

EXAMPLE 3

SELDI-TOF-MS Spectrum of Urinary Exosomes from Patients

Urinary exosomes from patients of various groups are analyzed by SELDI-TOF-MS. The results are confirmed by LC-MS/MS. Spectrum of SELDI-TOF-MS from representative patients is shown in FIGS. 2-6. Table 1 summarizes proteins that were detected by SELDI-MS and confirmed by LC-MS/MS in different test groups.

TABLE 1

Proteins detected in urine samples by SELDI-MS

| Patient | MW | Protein |
|---|---|---|
| HIVAN | 10,585 | HIV envelope gp; HIV Protease |
|  | 23,546 | HIV envelope gp; HIV Nef; HIV Vif |
|  | 33,464 | HIV protein gp; mu A03009B12Rik Protein |
|  | 45,632 | HIV envelope gp; HIV pol protein |
|  | 66,587 | HIV envelope gp; HIV Nef; PgD synthase |
|  | 78,942 | Unknown |
| AA HIV | 23,684 | HIV envelope gp; HIV Nef; PgD synthase |
|  | 83,256 | Unknown |
| FSGS | 66,533 | Unknown |
| White HIV | 23,935 |  |

Table 2 summarizes the urine protein profiles in individual patient.

TABLE 2

Urine protein profiles in individual patient

| ID | Diagnosis | Race | CD4 | VL | Nef | Gag | Pol | Protease | Rev | RT | Tat | Vif | p1 | p24 | P17 | poly |
|---|---|---|---|---|---|---|---|---|---|---|---|---|---|---|---|---|
| 22 | HIV AN | AA |  |  | X | X | X | X | X |  | X | X | X | X | X |  |
| 27 | HIV/AIDS | AA | 134 | <50 | X |  |  |  |  |  |  |  |  |  |  |  |
| 28 | HIV/AIDS | AA | 134 | 19,800 | X | X |  | X |  | X |  | X |  |  |  |  |
| 30 | HIV/AIDS | AA | <20 | >10,000 | X | X | X | X |  | X | X | X |  | X | X | X |
| 41 | HIV | AA | 440 | 29,187 | X | X | X |  |  |  |  |  |  |  |  |  |
| 46 | HIV | AA | 689 | <50 |  | X | X |  | X | X |  |  |  |  |  |  |
| 62 | HIV | AA | 232 | <50 | X |  |  |  |  |  |  |  |  |  |  |  |
| 63 | HIV/AIDS | AA | 83 | 2,023 | X |  |  |  |  |  |  |  |  |  |  |  |
| 70 | HIV | AA | 990 | <50 | X |  |  |  |  |  |  |  |  |  |  |  |
| 104 | HIV | AA | 313 | 77 | X | X |  |  |  |  |  |  |  |  |  |  |
| 111 | HIV/AIDS | AA | 182 | <50 |  | X | X |  |  |  |  |  |  |  |  |  |
| 112 | HIV | AA | 584 | >200 |  |  | X |  |  | X |  |  |  |  |  |  |
| 48 | HIV | W | 454 | 52000 | X |  |  |  | X |  | X | X |  |  |  |  |
| 86 | HIV | W | 1642 | <75 | X | X | X | X |  |  |  |  |  |  |  |  |
| 103 | HIV | W | 560 | 150 | X | X | X |  |  |  |  |  |  |  |  |  |
| 106 | HIV | W | 302 | <50 |  |  |  |  |  |  |  |  |  |  |  |  |
| 108 | HIV | W | 653 | <50 | X | X | X |  |  |  |  |  |  |  |  |  |
| 110 | HIV | W | 379 | <50 | X | X |  |  |  |  |  |  |  |  |  |  |

Transmission Electron Microscopy (TEM)

TEM was used to visualize the patients' vesicles from urine. Exosomes were isolated from 4 ml of urine, fixed and embedded for TEM. The figure shows distribution of vesicles in: A) HIVAN; B) focal segmental glomerusclerosis; C) AA HIV+; and D) white HIV+; E) AA HIV negative. HIVAN, FSGS and AA HIV+ patients clearly have a higher population of vesicles compared to white HIV+ patients and AA normal patients.

Ingenuity Pathways Analysis

As shown in Examples 1 and 2, the SELDI-TOF-MS peaks of AA HIV+ patients exhibited exceedingly similar protein patterns to those of HIVAN patients and slightly similar patterns to FSGS patients, suggesting that the AA HIV+ patients whose peaks were similar to those of HIVAN may be predisposed to developing HIVAN. The baseline protein value (30-2000 mg/dl) for the FSGS patients and AA HIV+ patients was in the same range. Similar to the protein values for HIVANb, but unlike FSGS patients, the proteins detected in AA HIV+ patients were analogous to those of HIVAN patients. This underscores the significance that HIV infection, with or without the presence of renal disease, is still largely responsible for development of HIVAN; and a prior condition of renal insufficiency before HIV infection is not a necessary prerequisite for the development of HIVAN.

Unlike AA HIV+ patients, protein profiles of white HIV+ patients were a stark contrast to the protein profiles of HIVAN patients. It suggests that factors other than simple infection of renal cells or the infiltration of infected immune cells in renal tissue probably mediate the expression of nephropathy. The number of AA HIV+ and HIVAN ($12/15$) patients that had detectable Nef using LC-MS/MS piggybacks on the earlier assertion about the similarities between the kidney pathologies of transgenic mice expressing Nef and HIVAN patients, hinting that Nef may be involved in causing kidney damage to HIV patients. This may explicate the relationship, if any, between the similarity in the kidney pathology of transgenic mice expressing Nef and HIVAN patients, and the similarity between the expression of Nef in the protein profiles of AA HIV+ and HIVAN patients. It may also shed additional insight as to what role Nef plays in the pathogenesis of HIVAN. HIV envelope gp was also detected by LC-MS/MS in HIVAN and AA HIV+ patients. Although local HIV infection of the kidney may have implications beyond development of HIVAN, with kidney serving as a potential viral reservoir, a corollary would be that some of these viruses in the reservoir would find their way in the urine.

The transmission electron microscopy (FIG. 7) shown in the urine of AA HIV+, FSGS and HIVAN patients' conspicuous vesicles were not evident in the urine of white HIV+ and AA normal patients. The HIVAN exosome solution was diluted 10 fold because the initial visualization expressed an exceedingly dense population of exosomes that was difficult to visualize, suggesting that HIVAN patients may be producing vesicles at an increasing rate than all the other patient groups. The HIV-associated kidney damage may responsible for this marked increase in exosome excretion in AA HIV+ and HIVAN patients.

EXAMPLE 4

Figure 8:
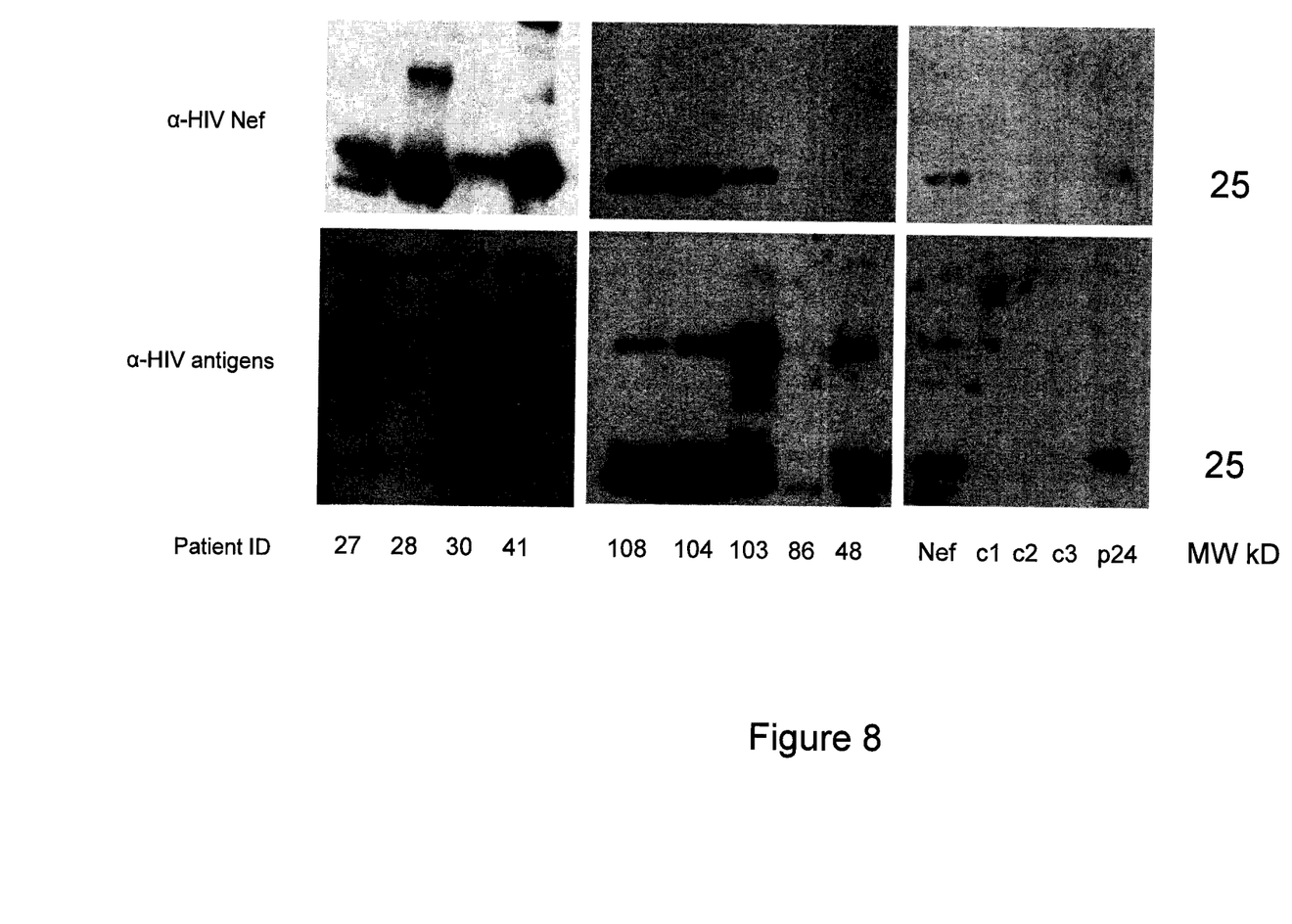
FIG. 8 is a composite of pictures showing Western blot analysis of urinary vesicles from HIV+ patients and controls. Vesicles were isolated from urine by ultrafiltration and analyzed for the presence of HIV Nef or other HIV proteins. The top panel used anti-HIV Nef monoclonal antibodies, while the lower panel utilized pooled HIV+ patient sera s the primary antibodies. Patients 27, 28, 30, 41 and 104 were AA. Patients 108, 103, 86 and 48 were HIV+ white patients. The last panel is control panel for three HIV negative individuals, recombinant HIV Nef and p24.

Western Blot Analysis, Validation of the Presence of HIV Nef and Other HIV Proteins Urinary vesicle samples from fourteen (14) HIV+ AA and nine (9) HIV+ white patients were isolated using ultrafiltration and analyzed for the presence of HIV Nef and other HIV proteins using western blot analysis. All the HIV+ AA samples were positive for HIV Nef by western blot, although HIV Nef was not detected in sample 41 by mass spectrometry (FIG. 8). This discrepancy could be caused by the isolation method utilized for the mass spectrometry analysis, which was ultracentrifugation, and yields less protein. HIV Nef was only identified in four (4) HIV+ white patients while mass spectrometry identified three (3) samples without HIV Nef. All HIV+ patients had detectable HIV proteins by western blots, but had varying kinds and amounts (FIG. 8).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The embodiments are intended to cover the components and steps in any sequence which is effective to meet the objectives there intended, unless the context specifically indicates the contrary.

What is claimed is:

1. A kit for detecting HIV proteins in urine exosomes, comprising:
    a centrifuge filter for isolating exosomes, having a pore size smaller than the size of exosomes, wherein said exosomes are 50-90 nm vesicles;
    at least one anti-HIV antibody directed against Nef, gp120, gp41, Rev, reverse transcriptase, Tat or Pol; and
    at least one HIV biomarker protein standard selected from the group consisting of Nef, gp120, gp41, Rev, reverse transcriptase, Tat and Pol.

2. The kit of claim 1, comprising anti-HIV antibodies against each of Nef and Pol.

3. The kit of claim 1, comprising each of the HIV biomarker protein standards, Nef and Pol.

4. The kit of claim 1, further comprising reagents suitable for detecting the formation of an immune complex between said at least one anti-HIV antibody and one or more HIV antigens selected from the group consisting of Nef and Pol.

5. The kit of claim 1, further comprising a container suitable for collecting a urine sample.

6. The kit of claim 1, wherein the centrifuge filter has a molecular weight cutoff between 50 kd and 500 kd.

7. The kit of claim 1, further comprising an exosome resuspension solution.

8. The kit of claim 1, wherein the exosome resuspension solution is phosphate buffered saline.

* * * * *